United States Patent [19]

Atkinson et al.

[11] Patent Number: 4,822,803
[45] Date of Patent: Apr. 18, 1989

[54] BENZOFURAN 2-CARBOXYLIC ACID HYDRAZIDES USEFUL AS INHIBITORS OF LEUKOTRIENE BIOSYNTHESIS

[75] Inventors: Joseph G. Atkinson, Montreal; Yvan Guindon, Ile Bizard; Cheuk K. Lau, Pierrefonds, all of Canada

[73] Assignee: Merck Frosst Canada, Inc., Quebec, Canada

[21] Appl. No.: 152,215

[22] Filed: Feb. 4, 1988

Related U.S. Application Data

[60] Division of Ser. No. 1,262, Jan. 7, 1987, Pat. No. 4,745,127, which is a division of Ser. No. 725,265, Apr. 19, 1985, Pat. No. 4,663,347, and a continuation-in-part of Ser. No. 800,624, Nov. 21, 1985, abandoned, which is a continuation of Ser. No. 584,061, Feb. 27, 1984, abandoned, and a continuation-in-part of Ser. No. 661,645, Oct. 17, 1984, abandoned, which is a continuation-in-part of Ser. No. 547,508, Oct. 31, 1983, abandoned.

[51] Int. Cl.$^4$ .................. A61K 31/34; C07D 307/85
[52] U.S. Cl. .................. 514/320; 514/463; 514/469; 540/480; 540/596; 546/196; 548/525; 549/361; 549/387; 549/433; 549/458; 549/467
[58] Field of Search .............. 549/361, 387, 433, 458, 549/467; 546/196; 548/525; 540/480, 596; 514/212, 320, 422, 452, 454, 463, 468, 469

[56] References Cited

U.S. PATENT DOCUMENTS

| | | | |
|---|---|---|---|
| 3,557,152 | 1/1971 | Zergenyi et al. | 549/460 |
| 3,574,208 | 4/1971 | Zergenyi et al. | 424/285 |
| 3,627,785 | 12/1971 | Zergenyi et al. | 549/468 |
| 3,646,047 | 2/1972 | Wright et al. | 546/196 |
| 3,651,094 | 3/1972 | Libis et al. | 549/468 |
| 3,665,074 | 5/1972 | Brandstrom et al. | 549/467 |
| 3,674,810 | 7/1972 | Zergenyi et al. | 549/468 |
| 3,723,619 | 3/1973 | Zergenyi et al. | 424/285 |
| 3,830,929 | 8/1974 | Nordmann et al. | 549/467 |
| 3,915,687 | 10/1975 | Braunling et al. | 71/88 |
| 4,055,117 | 10/1977 | Munday | 107/11 |
| 4,085,117 | 4/1978 | Cragoe, Jr. et al. | 549/468 |
| 4,100,294 | 7/1978 | Cragoe, Jr. et al. | 424/275 |
| 4,213,998 | 7/1980 | Witiak | 424/285 |
| 4,221,793 | 9/1980 | Weber et al. | 544/376 |
| 4,229,467 | 10/1980 | Parker | 424/285 |
| 4,424,231 | 1/1984 | Bantick et al. | 549/468 |

FOREIGN PATENT DOCUMENTS

| | | |
|---|---|---|
| 671060 | 4/1966 | Belgium . |
| 19955 | 12/1980 | European Pat. Off. . |
| 45473 | 2/1982 | European Pat. Off. . |
| 73663 | 3/1983 | European Pat. Off. . |
| 69521 | 11/1983 | European Pat. Off. . |
| 123543 | 10/1984 | European Pat. Off. . |
| 1212984 | 3/1966 | Fed. Rep. of Germany . |
| 2909754 | 9/1980 | Fed. Rep. of Germany . |
| 2231372 | 2/1974 | France . |
| 50-35310 | 4/1975 | Japan . |
| 50-049270 | 5/1975 | Japan . |
| 56039015 | 9/1979 | Japan . |
| 57-040479 | 3/1982 | Japan . |
| 500966 | 2/1971 | Switzerland . |
| 540900 | 8/1973 | Switzerland . |
| 399106 | 9/1973 | U.S.S.R. . |
| 1008260 | 4/1968 | United Kingdom . |
| 1233268 | 5/1971 | United Kingdom . |
| 1464242 | 7/1977 | United Kingdom . |
| 2007973 | 5/1979 | United Kingdom . |
| 2118552 | 3/1980 | United Kingdom . |

OTHER PUBLICATIONS

Kumar et al., Chem. Abstracts, vol. 73 (1970) 25209v.
Fujiwara et al., J. Org. Chem., 46, 851 (1981).
Chem. Abstracts, 65, 18546h.
Chem. Abstracts, 58, 13881c.
Chem. Ber., 99 (6), 2063–2065 (1966).
Rodighiero and Fornasiero, Gazz. Chim. Ital., 91, 90–102 (1961).
Die Pharmazie 35, No. 9, pp. 517–539, (Sep. 1980).
Rene Royer et al., Eur. J. Med. Chem. Chimica Therapeutica, Mar.–Apr. 1974–9, No. 2, pp. 136–145.
W. B. Whalley, J. Chem. Soc., pp. 3229–3235 (1951).
Grinev et al., C.A. 93:26184h.
Gaevoi, V. P., C.A. 96:79444m.

*Primary Examiner*—Mary Lee
*Assistant Examiner*—Bernard I. Dentz
*Attorney, Agent, or Firm*—Gabriel Lopez; Hesna J. Pfeiffer

[57] ABSTRACT

Compounds of the Formula I:

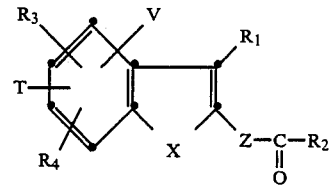

and pharmaceutically acceptable salts thereof are inhibitors of leukotriene biosynthesis. These compounds inhibit the mammalian 5-lipoxygenase enzyme, thus preventing the metabolism of arachidonic acid to the leukotrienes. These compounds are thus useful in the treatment of asthma, allergic disorders, inflammation, skin diseases and certain cardiovascular disorders.

8 Claims, No Drawings

BENZOFURAN 2-CARBOXYLIC ACID HYDRAZIDES USEFUL AS INHIBITORS OF LEUKOTRIENE BIOSYNTHESIS

This application is a division of Ser. No. 001,262, filed Jan. 7, 1987, now U.S. Pat. No. 4,745,127, which is a division of Ser. No. 725,265, Apr. 19, 1985, now U.S. Pat. No. 4,663,347, and a continuation-in-part of Ser. No. 800,624, filed Nov. 21, 1985, now abandoned, which is a continuation of Ser. No. 584,061, filed Feb. 27, 1984, now abandoned, and a continuation-in-part of Ser. No. 661,645, filed Oct. 17, 1984, now abandoned, which is a continuation-in-part of Ser. No. 547,508, filed Oct. 31, 1983, now abandoned.

This invention is directed to pharmaceutical compositions containing a compound of the Formula I:

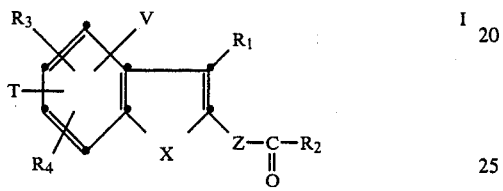

and pharmaceutically acceptable salts thereof wherein the various substituents are as defined herein below:

Z is a bond, $CR_{14}=CR_{15}$ or $CHR_{14}-CHR_{15}$;

X is O, S, SO, or $SO_2$;

$R_2$ is H, OH, $C_1$ to $C_{20}$ alkoxy, including straight chain or branched chain, cycloalkyl, bicycloalkyl, tricycloalkyl or tetracycloalkyl; $Ar_1-C_1$ to $C_3$ alkoxy; $NR_8Ar_1$, wherein $R_8$ and $Ar_1$ can optionally be joined to form a heterocyclic ring having 5 to 8 ring atoms; $-NR_8Het$; $-N(R_8)CH_2Ar_1$; $-N(R_{13})-N(R_{13})_2$ wherein each $R_{13}$ is independently hydrogen, $R_8$, $R_9$, $Ar_1$ or Het; $-NH-CH=C(Ar_1)_2$; $-O(CH_2)_nNR_8R_9$ wherein n is 2 to 4; $-Z-Ar_1$;

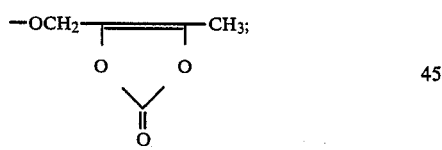

—lower acyloxy-lower alkoxy (e.g.

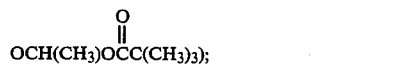

$-CH_2OH$; $-(CH_2)_nAr_1$ wherein n is 0 to 3; $-(CH_2)_nCOOR_6$ wherein n is 0 to 6; $C_1$ to $C_{20}$ alkyl; $Ar_1$; Het; $(CH_2)_nNR_8R_9$ wherein n is 1 to 3; or Het;

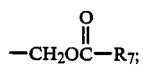

and $R_1$, $R_3$, $R_4$, T and V are each independently selected from:
(1) hydrogen;
(2) alkyl having 1 to 6 carbon atoms;
(3) alkenyl having 2 to 6 carbon atoms;

(4) $-(CH_2)_nM$ wherein
n is 0 to 6 except when X is S and M is $OR_5$, in which case n is 1 to 6 and
M is
(a) $-OR_5$;
(b) halogen;
(c) $-CF_3$;
(d) $-SR_5$;
(e) $Ar_1$;
(f) $-COOR_6$;
(g)

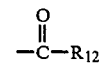

wherein $R_{12}$ is H, $C_1$ to $C_6$ alkyl, or $Ar_1$;
(h) tetrazole;
(i)

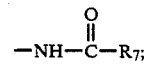

(j)

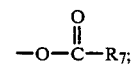

(k)

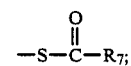

(l)

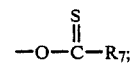

(m) $-NR_8R_9$;
(n) $-NHSO_2R_{10}$ wherein $R_{10}$ is OH, $C_1$ to $C_6$ alkyl, $CF_3$, $C_1$ to $C_6$-alkoxy, or $Ar_1$;
(o)

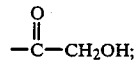

(p) $-SOR_5$;
(q) $-CONR_8R_9$;
(r) $-SO_2NR_8R_9$;
(s) $-SO_2R_5$;
(t) $-NO_2$; or
(u) $-CN$;

or any two of $R_3$, $R_4$, T and V may be joined to form a saturated ring having 5 or 6 ring atoms, said ring atoms comprising 0, 1 or 2 atoms selected from oxygen and sulfur, the remaining ring atoms being carbon;

each $R_5$ is independently H, $C_1$ to $C_6$ alkyl, benzyl, $Ar_1$, perfluoro-$C_1$ to $C_4$ alkyl, $CH_2-R_{11}$ wherein $R_{11}$ is $C_1$ to $C_5$ alkyldimethylamino, hydroxy-$C_2$ to $C_5$ alkyl, $CH_2COOR_6$, or $CH_2CO-R_7$;

each $R_6$ is independently H or $C_1$ to $C_6$ alkyl;

each $R_7$ is independently $C_1$ to $C_6$ alkyl, benzyl, $Ar_1$, $NR_8R_9$, $NHAr_1$, or $O-C_1$ to $C_4$ alkyl;

each $R_8$ and each $R_9$ is independently H or $C_1$ to $C_4$ alkyl, or $R_8$ and $R_9$ may be joined through the N to which they are attached to form a heterocycloalkyl ring having 5 to 8 ring atoms;

each Het is independently an aromatic heterocyclic ring having 5 or 6 ring atoms, one or more of which are selected from N, O and S;

each $Ar_1$ is independently 1- or 2- naphthyl, phenyl or mono- or disubstituted phenyl, wherein the substituents on the phenyl are independently selected from $C_1$ to $C_3$ alkyl, I, Br, Cl, F, $COOR_6$, $(CH_2)_n$—$NR_8R_9$ wherein n is 0 to 2, methylenedioxy, $C_1$ to $C_3$ alkoxy, OH, CN, $NO_2$, $CF_3$, $C_1$ to $C_4$ acyl, $NR_8R_9$, S—$C_1$ to $C_6$ alkyl, SO—$C_1$ to $C_6$ alkyl, and $SO_2$—$C_1$ to $C_6$ alkyl; and $R_{14}$ and $R_{15}$ are each independently H or $C_1$ to $C_6$ alkyl.

This invention also provides a method of treatment for disease states caused by the synthesis of the Leukotrienes $C_4$, $D_4$, $E_4$ and $F_4$, as well as Leukotriene $B_4$, in mammals especially in a human subject. This method comprises administering to said subject an effective amount of a compound of Formula I combined with an appropriate pharmaceutical carrier.

The compounds of Formula I may be used to treat or prevent mammalian (especially human) disease states such as erosive gastritis; erosive esophagitis; inflammatory bowel disease; ethanol-induced hemorrhagic erosions; hepatic ischemia; noxius agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

Finally, this invention also provides novel compounds within the Formula I that act as inhibitors of the mammalian 5-lipoxygenase enzyme system, thus preventing the biosynthesis of the Leukotrienes $C_4$, $D_4$ and $E_4$ and also Leukotriene $B_4$. U.S. Pat. No. 4,663,347 (Atkinson et al.) is incorporated herein by reference in its entirety.

What is claimed is:

1. A compound of the formula:

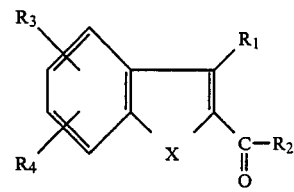

wherein the substituents for a compound are selected from the following groups:

| Compound | X | $R_1$ | $R_2$ | $R_3$ | $R_4$ |
|---|---|---|---|---|---|
| 116 | O | $CH_3$ | —NHNHPh—p-$NO_2$ | 6-OH | H |
| 117 | O | $CH_3$ | —NHNHPh | 4-OH | H |
| 118 | O | $CH_3$ | —NHNHPh—p-OMe | 5-OH | H |
| 119 | O | $CH_3$ | —NHNHPh—p-OMe | 4-OH | H |
| 120 | O | $CH_3$ | —NHNHPh—p-OMe | 4-OAc | H |
| 121 | O | $CH_3$ | —NHNHPh—p-$NO_2$ | 4-OH | H |
| 122 | O | $CH_3$ | —NHNHPh—p-$NO_2$ | 4-OAc | H |
| 123 | O | $CH_3$ | N(H)—N(piperidinyl) | 4-OAc | H |
| 124 | O | $CH_3$ | NHNHPh—p-Cl | 4-OAc | H |
| 125 | O | $CH_3$ | NHNHPh—p-Cl | 6-OH | H |
| 126 | O | $CH_3$ | NHNHPh—p-Cl | 4-OH | H |
| 127 | O | $CH_3$ | NHNHPh—p-Cl | 4-O-C(=O)-OMe | H |
| 128 | O | $CH_3$ | NHNHPh—m-OMe | 4-OH | H |
| 129 | O | Ph | NHNHPh—p-OMe | 6-OAc | H |
| 130 | O | $CH_3$ | NHNHPh—p-Cl | 5,6-$OCH_2O$— | H |
| 131 | O | $CH_3$ | NHNHPh—p-Cl | 5-OAc | 6-OAc |
| 132 | O | $CH_3$ | NHNHPh—p-Cl | 5-OH | 6-OH |
| 133 | O | $CH_3$ | NHNHPh—p-OMe | 4-O-CH($CH_3$)-OH | H |
| 135 | O | $CH_3$ | NHNHPh | 4-O-C(=O)-C($CH_3$)$_3$ | H |
| 136 | O | Ph | NHNHPh—p-OMe | 6-OH | H |
| 137 | O | $CH_3$ | NHNHPh—3,4-$Cl_2$ | 4-OH | H |
| 138 | O | $CH_3$ | —NMeNMePh | 4-OH | H |
| 139 | O | $CH_3$ | —NMeNMePh | 4-OAc | H |
| 140 | O | $CH_3$ | NHNHPh—3,4-$Cl_2$ | 4-OAc | H |

-continued

| Compound | X | R₁ | R₂ | R₃ | R₄ |
|---|---|---|---|---|---|
| 141 | O | CH₃ | (see structure below) | 4-OAc | H |
| 142 | O | CH₃ | NHNHPh—p-Cl | 5-OAc | H |
| 143 | O | CH₃ | NHNHPh—p-Cl | 5-OH | H |
| 144 | O | CH₃ | NHNHPh—m-OMe | 4-OAc | H |
| 145 | O | CH₃ | NHNHPh | 4-OC(O)OMe | H |
| 146 | O | CH₃ | NHNHPh—p-OMe | 4-OH | 5-Pr |
| 147 | O | CH₃ | NHNHPh—p-OMe | 4-CH₂CH=CH₂ | 5-OAc |
| 148 | O | Pr | NHNHPh—p-OMe | 4-OC(O)OMe | H |
| 149 | O | Pr | NHNHPh—p-OMe | 6-OAc | H |
| 150 | O | Pr | NHNHPh—p-OMe | 6-OH | H |
| 151 | O | CH₃ | —NEtNHPh | 4-OAc | H |
| 152 | O | CH₃ | —NEtNHPh | 4-OH | H |
| 153 | O | CH₃ | —NHNHPh—p-OMe | 5-OC(O)OMe | H |
| 154 | O | CH₃ | —NHNHPh—p-Cl | 5-OC(O)OMe | H |
| 155 | O | CH₃ | —NHNHPh—p-OMe | 4-OC(O)OMe | 5-CH₂CH=CH₂ |
| 156 | O | CH₃ | NMeNMePh | 4-OC(O)OMe | H |
| 157 | O | CH₃ | NHNHPh—p-Cl | 4-OC(O)OEt | H |
| 158 | O | CH₃ | NHNHPh—p-OMe | 4-OC(O)OMe | 5-Pr |
| 159 | O | CH₃ | NHNHPh—3,4-Cl₂ | 4-OC(O)OCH₃ | H |
| 160 | O | CH₃ | NHNHPh—p-Cl | 4-OC(O)OCH₂CH(CH₃)₂ | H |
| 161 | O | CH₃ | NHNHPh—p-OMe | 4-OC(O)OMe | H |

Structure for compound 141: a furan ring bearing CH₃ groups with a C(=O)NHNH-aryl (3,4-dichlorophenyl) substituent and a 2-methyl-6-acetoxyphenyl group.

-continued

| Compound | X | $R_1$ | $R_2$ | $R_3$ | $R_4$ |
|---|---|---|---|---|---|
| 269 | O | $CH_3$ | —NMeNMePh—p-F | 5-OH | 6-OH |
| 270 | O | $CH_3$ | —NHNMePh—p-F | 5-OH | 6-OH |
| 271 | O | $CH_3$ | —NHNMePh—p-Cl | 5-OH | 6-OH |
| 272 | O | $CH_3$ | —NHNMePh—p-Cl | 5-OH | 6-OH |
| 273 | O | $CH_3$ | —NHNMePh—p-F | 4-OH | H |
| 274 | O | $CH_3$ | —NMeNMePh—p-F | 4-OH | H |
| 279 | O | $CH_3$ | —NHNMePh—p-$CF_3$ | 4-OH | H |
| 285 | O | $CH_3$ | —NHNMePh—p-F | 4-OH | 5-Pr |
| 286 | O | $CH_3$ | —NHNMePH—p-F | 5-OH | H |
| 287 | O | $CH_3$ | —NHNMePh | 4-OH | H |

2. A compound of claim 1 which is: 117–133, 135–161, or 287.

3. A compound of claim 1 which is: 117, 126, 127, 132, 138, 146, or 154.

4. A compound of the Formula Ic:

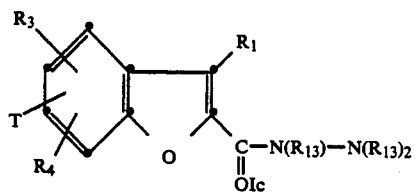

wherein
$R_1$ is hydrogen, $C_1$ to $C_6$ alkyl, $Ar_1$—$C_1$ to $C_3$ alkyl, $Ar_1$ or $CH_2OH$;
$R_3$, $R_4$ and T are each independently selected from:
(1) hydrogen;
(2) alkyl having 1 to 4 carbon atoms;
(3) alkenyl having 2 to 4 carbon atoms;
(4) —$(CH_2)_nM$ wherein
n is 0 or 1, and
M is
(a) —$OR_5$;
(b) halogen;
(c) —$CF_3$;
(d) —$SR_5$;
(e) $Ar_1$;
(f) —$COOR_6$;
(g)

wherein $R_{12}$ is H, $C_1$ to $C_6$ alkyl, or $Ar_1$;
(h)

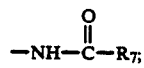

(i)

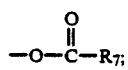

(j)

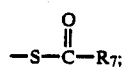

(k)

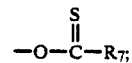

(l) $NR_8R_9$;
(m) —$NHSO_2R_{10}$ wherein $R_{10}$ is $C_1$ to $C_6$ alkyl, phenyl, p-tolyl or $CF_3$;
(n) —$SOR_5$;
(o) —$CONR_8R_9$;
(p) —$SO_2NR_8R_9$;
(q) —$SO_2R_5$;
(r) k—$NO_2$; or
(s) —CN;

or any two of $R_3$, $R_4$ and T may be joined to form a saturated ring having 5 or 6 ring atoms, said ring atoms comprising 0, 1 or 2 oxygen atoms, the remaining ring atoms being carbon;

each $R_5$ is independently H, $C_1$ to $C_6$ alkyl, benzyl $Ar_1$, perfluoro-$C_1$-$C_4$ alkyl, $CH_2$—$R_{11}$ wherein $R_{11}$ is hydroxy $C_2$ to $C_5$ alkyl, $CH_2COOR_6$, or $CH_2CO$—$R_7$;

each $R_6$ is independently H or $C_1$ to $C_6$ alkyl;

each $R_7$ is independently $C_1$ to $C_6$ alkyl, benzyl, $Ar_1$, $NR_8R_9$, $NHAr_1$, O—$C_1$ to $C_4$ alkyl;

each $R_8$ and each $R_9$ is independently H or $C_1$ to $C_4$ alkyl, or $R_8$ and $R_9$ may be joined through the N to which they are attached to form a heterocycloalkyl ring having 5 to 8 ring atoms;

each $R_{13}$ is independently hydrogen, $R_8$, $R_9$, or $Ar_1$, and each $Ar_1$ is independently 1- or 2-naphthyl, phenyl or mono- or disubstituted phenyl, wherein the substituents on the phenyl are independently selected from $C_1$ to $C_3$ alkyl, I, Br, Cl, F, $COOR_6$, $(CH_2)_n$—$NR_8R_9$ wherein n is 0 to 2, methylenedioxy, $C_1$ to $C_3$ alkoxy, OH, CN, $NO_2$, $CF_3$, $C_1$ to $C_4$ acyl, $NR_8R_9$, S—$C_1$ to $C_6$ alkyl, SO—$C_1$ to $C_6$ alkyl, and $SO_2$—$C_1$ to $C_6$ alkyl; with the proviso that at least one of the $R_{13}$ groups in the Formula Ic is $Ar_1$, and one of $R_3$, $R_4$ and T is $OR_5$ or —$OCOR_7$;

or a pharmaceutically acceptable salt thereof.

5. A method of inhibiting mammalian leukotriene biosynthesis or actin which comprises administering to a mammal in need of such treatment a pharmaceutically effective amount of a compound of claim 1.

6. A method of claim 5 wherein the mammal is a human.

7. A method of treating pulmonary conditions, inflammation, allergies, pain, cardiovascular conditions, or skin conditions which comprises administering to a human in need of such treatment a pharmaceutically effective amount of a compound of claim 1.

8. A pharmaceutical composition useful for inhibiting the biosynthesis of mammalian leukotrienes comprising a pharmaceutically acceptable carrier and an effective amount of a compound of claim 1.

* * * * *